United States Patent [19]

MacKay et al.

[11] 4,065,502
[45] Dec. 27, 1977

[54] CERTAIN β-DIKETONES AND THE USE THEREOF AS METAL EXTRACTANTS

[75] Inventors: Kenneth D. MacKay, Circle Pines; Edgar R. Rogier, Minnetonka, both of Minn.

[73] Assignee: General Mills Chemicals, Inc., Minneapolis, Minn.

[21] Appl. No.: 636,773

[22] Filed: Dec. 1, 1975

Related U.S. Application Data

[62] Division of Ser. No. 391,432, Aug. 24, 1973.

[51] Int. Cl.$^2$ ............................................. C07C 49/76
[52] U.S. Cl. ............................... 260/590 R; 260/592; 260/465 D; 260/465 G; 423/34
[58] Field of Search ........................... 260/590 R, 592

[56] References Cited

U.S. PATENT DOCUMENTS

| | | | |
|---|---|---|---|
| 2,313,621 | 3/1943 | Bruson | 260/590 R |
| 2,659,711 | 11/1953 | Wilkins et al. | 260/592 |
| 2,864,850 | 12/1958 | Westfahl | 260/590 R |
| 3,047,375 | 7/1962 | Pellegrini | 260/592 |
| 3,082,071 | 3/1963 | Hartle et al. | 260/592 |
| 3,742,062 | 6/1973 | Chappelow et al. | 260/592 |

OTHER PUBLICATIONS

Hampton et al., J. Org. Chem., vol. 31, pp. 1035–1038 (1966).
Stary, The Solvent Extraction of Metal Chelates, pp. 51–79, (1965).

Primary Examiner—James O. Thomas, Jr.
Assistant Examiner—James H. Reamer
Attorney, Agent, or Firm—Gene O. Enockson; Patrick J. Span

[57] ABSTRACT

New β-diketones of the structure

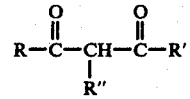

where R is phenyl or alkyl substituted phenyl, R' is alkyl, alkyl substituted phenyl or chloro substituted phenyl and R" is H or —CN with the provisos that; (1) when R is phenyl, R' is a branched chain alkyl group of at least seven carbon atoms and (2) when R is alkyl substituted phenyl, the number of carbon atoms in the alkyl substituent or substituents is at least 7 and at least one such alkyl substituent is branched chain. Process of recovering copper and nickel from their aqueous solutions by the use of the new β-diketones.

3 Claims, No Drawings

CERTAIN β-DIKETONES AND THE USE THEREOF AS METAL EXTRACTANTS

This application is a division of application Ser. No. 391,432, filed Aug. 24, 1973.

The invention relates to new β-diketone and to the use of same as metal extractants.

Liquid ion exchange recovery of metal values from aqueous solutions is rapidly reaching extensive commercial acceptance. Such processing has been described as being deceptively simple since all that is really happening is the transfer of a metal value from Phase A (aqueous) to Phase B (organic) and thence from Phase B to Phase C (aqueous). However complexities of liquid ion exchange arise in a number of areas including (1) synthesis and manufacture of the reagent system, (2) evaluation of the system's capabilities, and (3) engineering application leading to large scale metal recovery.

The key to a successful application of liquid ion exchange is the reagent. In this respect, the reagent should meet a number of criteria. In the first instance, the reagent must complex with or react with a metal or group of metals. It is also desirable that the reagent shows preference for a single metal where the aqueous starting solutions contain a number of metal values. The reagent should also desirably complex or react quantitatively with the metal under the extraction conditions. Additionally, the reagent, as well as the resulting metal complex, must exhibit satisfactory solubility in practical solvents. Further, the reagent-metal reaction must be reversible so that the metal can be stripped. For economic reasons, the reagent must be acceptably stable so that it can be recycled repeatedly. Also, it should be essentially water insoluble to prevent significant loss into the aqueous phase. Furthermore, the reagent should not cause or stabilize emulsions. And, of course, the cost of the reagent should be such that the liquid ion exchange process can be operated at a profit. Very few compounds have as yet found significant commercial acceptance.

Certain β-diketones have heretofore been proposed as reagents in liquid ion exchange processes. However, a check of the acceptability of a number of the proposed compounds showed that they did not satisfactorily meet one or more of the criteria outlined above. A major deficiency noted was the lack of requisite solubility in practical solvents, i.e. those boiling above about 150° C. Such solvents are needed for commercial practices from the standpoints of safety and reduction of evaporation loss.

Our new compounds have acceptable solubility in practical, commercially usable solvents. The metal complexes thereof also have acceptable solubility. Further, the new compounds extract satisfactory amounts of metals, namely copper and nickel. In this respect, an organic:aqueous phase ratio of 1:1 is considered to be ideal by some. This can be extended to somewhere in the neighborhood of 4 or 5 to 1 before the system becomes commercially unattractive. Typical ammoniacal copper leach feed solutions contain anywhere from 10 to 50 g./l. copper. At 0.5 Molar concentration in the organic, the new compounds of the invention can be used effectively at the indicated phase ratios to recover all or substantially all of the copper from the said ammoniacal solutions. Additionally the kinetics of extraction are unexpectedly good.

Another important property of the new compounds is their ability to extract metal values even where the leach solutions have relatively high ammonia concentrations. This can also be stated that such compounds are less sensitive to the amount of ammonia present in the copper feed solution than various of the heretofore suggested β-diketones. The cyano and chlorophenyl containing compounds of the invention are especially outstanding in this property.

The new compounds of the invention can be defined structurally as follows:

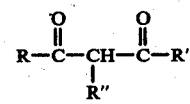

where R is phenyl or alkyl substituted phenyl, R' is alkyl, alkyl substituted phenyl or chloro substituted phenyl and R" is H or CN with the provisos that (1) when R is phenyl, R' is a branched chain alkyl group of at least seven carbon atoms and (2) when R is alkyl substituted phenyl, the number of carbon atoms in the alkyl substituent or substituents is at least 7 and at least one such alkyl substituent is branched chain. R is desirably monoalkyl substituted and preferably contains 9 or more carbon atoms. The various alkyl groups are preferably free from substitution and contain less than about 20 carbon atoms. Further, when R' is alkyl, the carbon α to the carbonyl group is desirably not tertiary.

The new compounds of the invention are prepared by known techniques. A preferred procedure is that generally described by Swamer and Houser in J. Amer. Chem. Soc., 72, 1352 (1950). Thus a lower alkyl ester is condensed with a compound containing an acetyl moiety in the presence of sodium hydride and an inert organic solvent. Typical inert organic solvents are diethyl ether and tetrahydrofuran.

The compound preparations can be further described by the following examples which are to be considered as illustrating preferred embodiments without being limiting.

EXAMPLE A

A dispersion of 16.9 g. (0.4 mole) of 57% by weight sodium hydride in mineral oil was slurried with n-pentane under nitrogen and the supernatant liquid was removed by suction through a sintered glass tip tube. The process was repeated three times before 500 ml. of dry diethyl ether was added at once. The mixture was slurried and 35.2 g. (0.4 mole) of ethyl acetate was rapidly added. Then about 2 ml. of dodecylacetophenone (the dodecyl group is branched chain and was derived from tetrapropylene via alkylation therewith) was added to the slurry. No gas evolution was indicated on a wet test meter, so two drops of absolute ethanol were added. After about an hour, vigorous gas evolution occurred and the remaining dodecylacetophenone was added as a 25% by weight solution in diethyl ether. The total ketone added was 57.6 g. (0.2 mole) and the addition was performed at such a rate as to maintain solvent reflux. When the addition was complete, the mixture was stirred until gas evolution ceased—1 to 2 hours. Another 150 ml. diethyl ether was added and the excess sodium hydride was neutralized by the careful addition of absolute ethanol. When the sodium hydride failed to react, the reaction mixture was poured onto a mixture of ice and conc. hydrochloric acid with vigorous stirring. The phases then were separated and the upper organic phase was washed twice with water, once with 10% sodium bicarbonate, and finally once with water. After drying over anhydrous magnesium sulfate, the solvent was distilled under reduced pressure. The product distilled at 96°-160° C. (0.5 mm. Hg.) and 39.2 g. of product was obtained (yield of 59%). The β-diketone product had the following structure (confirmed by its infrared spectrum):

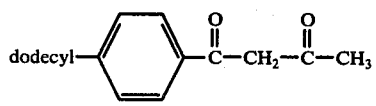

EXAMPLES B-K

The generalized reaction for preparing the compounds is as follows:

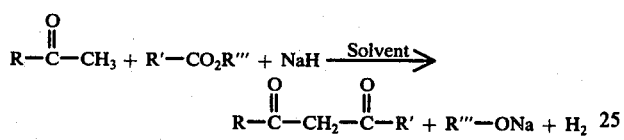

Examples B-K were carried out in essentially the same manner as Example A with the reactants, mole ratios and solvents set forth in the following Table A:

The process was repeated three times before 500 ml. of dry diethyl ether was added at once. The mixture was slurried and 60.8 g. (0.2 mole) of methyl dodecylbenzoate (the dodecyl group is as obtained in the alkylation of benzene with tetrapropylene) was rapidly added. Then 20.0 g. (0.2 mole) of pinacolone and two drops of methanol were rapidly added. Only a slow evolution of gas was observed on the wet test meter. After three days of continuous stirring, 7.5 l. of gas was evolved and the remaining sodium hydride was neutralized by the careful addition of absolute ethanol. When no further reaction was observed, the mixture was poured onto a mixture of ice and concentrated hydrochloric acid with vigorous stirring. The phases then were separated and the upper organic phase was washed twice with water, once with 10% sodium bicarbonate, and finally once with water. After drying over anhydrous magnesium sulfate, the solvent was distilled under reduced pressure. The product distilled at 110°-180° C. (0.3 mm. Hg.) and 54.1 g. of product was obtained. The infrared spectrum and gas-liquid chromatograph of the distillate indicated that 70% of it had the following structure,

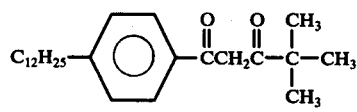

while the remainder was mostly methyl dodecylbenzoate.

Table A

| Example | R | R' | R''' | $RCCH_3$ (Mole Ratios) | $R'CO_2R'''$ | NaH | Solvent | % Yield | B. Pt. ° C. |
|---|---|---|---|---|---|---|---|---|---|
| B | $C_{12}H_{25}-\phi-$[8] | $C_8H_{17}$[1] | $C_2H_5$ | 0.2 | 0.4 | 0.4 | $Et_2O$ | 23 | 150-190 (0.2 mm.) |
| C | $C_{12}H_{25}-\phi-$ | $C_7H_{15}$[2] | $C_2H_5$ | 0.5 | 0.7 | 1.0 | $Et_2O$ | 65 | 190-240 (0.6 mm.) |
| D | $C_{12}H_{25}-\phi-$ | $(CH_3)_3O-\phi-$ | $C_2H_5$ | 1.0 | 1.2 | 2.2 | $Et_2O$ | 81 | —[3] |
| E | $\phi-$ | $C_{17}H_{35}-$[4] | $C_2H_5$ | 1.0 | 1.47 | 2.4 | $Et_2O$ | 39 | 205-212 (0.3 mm.) |
| F | $\phi-$ | $C_7H_{15}-$[2] | $C_2H_{15}$ | 1.0 | 1.4 | 2.4 | $Et_2O$ | 73 | 135-150 (0.5 mm.) |
| G | $C_9H_{19}-\phi-$[5] | $CH_3-$ | $C_2H_5$ | 1.0 | 1.2 | 2.2 | THF[6] | 85 | 155-162 (—) |
| H | $C_{12}H_{25}-\phi-$ | $CH_3-\phi-$ | $CH_3$ | 1.0 | 1.2 | 2.1 | THF | 97 | —[3] |
| I | $C_9H_{19}-\phi-$ | $CH_3-\phi-$ | $CH_3$ | 0.48 | 0.6 | 1.2 | THF | 74 | —[3] |
| J | $C_{12}H_{25}-\phi-$ | 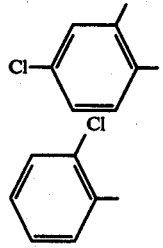 | $C_2H_5$ | 1.0 | 1.05 | 2.2 | $Et_2O$ | 75 | 250-260 (.02-.04 mm.)[7] |
| K | $C_{12}H_{25}-\phi-$ | Cl-phenyl (ortho-Cl) | $C_2H_5$ | 0.77 | 0.87 | 1.80 | $Et_2O$ | 71 | 235-250 (.13-.25 mm.)[7] |

[1]The octyl group is $(CH_3)_3CCH_2CHCH_3CH_2-$ and is derived from Isononanoic Acid (American Hoechst Corp.).
[2]The heptyl group is a mixture of isomeric dimethyl pentyl groups and is derived from Isooctanoic Acid (American Hoechst Corp.).
[3]Not possible to satisfactorily distill in a pot distillation. No molecular distillation attempted.
[4]Derived from Isostearic Acid (Emery Industries) - a mixture of isomeric, branched $C_{18}$ acids.
[5]The nonyl group is that obtained from alkylation of benzene with tripropylene.
[6]n-Heptane used to dissolve the β-diketone during the work-up of reactions where tetrahydrofuran was used as the reaction solvent.
[7]Wipe-film still distillation.

[8]The symbol "$\phi-$" designates a benzene ring, , and all alkyl groups are primarily in the para position.

EXAMPLE L

A dispersion of 16.9 (0.4 mole) of 57% by weight sodium hydride in mineral oil was slurried with n-pentane under nitrogen and the supernatant liquid was removed by suction through a sintered glass tip tube.

EXAMPLE M

A solution of 80.6 g. (0.195 mole) of the β-diketone of Example C in 1 l. of cyclohexane was shaken with an equal volume of aqueous solution containing 0.2 M copper sulfate, 0.5 M ammonia, and 0.5 M ammonium carbonate. After a few minutes of shaking, the phases were separated and the organic phase was shaken again with fresh aqueous solution. After phase separation, the copper rich organic phase was dried over anhydrous sodium sulfate. The sodium sulfate was removed by filtration.

A stream of cyanogen chloride gas was slowly bubbled through the solution of copper-$\beta$-diketone complex. Copious quantities of solids were precipitated during the addition. The reaction was followed by infrared spectroscopy and when the ratio of absorbances at 1615 cm$^{-1}$ to 2220 cm$^{-1}$ became constant at about 3.1, the addition was terminated. The time of addition was about two hours. A portion of the reaction mixture was clarified by filtration, the remainder was centrifuged. After decanting the supernatant, it was combined with the filtrate and washed twice with 3 N sulfuric acid. The organic phase was then dried over anhydrous sodium sulfate. The solvent was removed by distillation under reduced pressure leaving 79.5 g. (95% yield) of residue. A GLC analysis of the product indicated that it was at least 97% pure and infrared analysis confirmed the following structure:

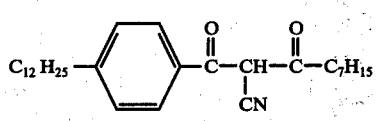

As indicated above the new compounds set forth herein are useful for the extraction of metals from aqueous solutions which extraction process also forms part of the invention. The compounds are particularly effective as extractants for copper and nickel from ammoniacal solutions thereof.

In the extraction recovery process, the new $\beta$-diketones are dissolved in an organic solvent boiling above about 150° C. and the solution is contacted with the aqueous metal containing solution to form a complex of the metal and the $\beta$-diketone. The organic phase is then separated from the aqueous phase and the metal values are stripped from the organic phase.

The high boiling organic solvents are essentially water immiscible and are preferably aliphatic hydrocarbons such as the petroleum derived liquid hydrocarbons, either straight or branched, such as kerosene, fuel oil, etc. In addition to the simple hydrocarbon solvents, chlorinated hydrocarbons may also desirably be used. Accordingly, both the unsubstituted and the chlorinated solvents are contemplated by the term "liquid hydrocarbon."

In the process of the invention, the new $\beta$-diketones are dissolved in the organic solvent in an amount sufficient to extract at least some of the metal values from their aqueous solution. Preferably, the $\beta$-diketones will be used in amounts of about 2 to 15% by weight based on the weight of the organic solvent.

The phase ratios can vary widely since the contacting of any quantity of the $\beta$-diketone solution with the metal containing aqueous phase will result in extraction of metal values into the organic phase. However, for commercial practicality, the organic:aqueous phase ratios are preferably in the range of 5:1 to 1:5. For practical purposes, the extractions (and stripping) are normally carried out at ambient temperatures and pressures. Thus there is no advantage in using high temperatures or pressures since any increase in extraction or the rate thereof would be off-set by the added costs of deviating from the temperature or pressure existing at the location of use. The entire process can be carried out continuously with the stripped organic solvent solution being recycled for contacting further quantities of metal containing solutions.

The loaded organic is preferably stripped using aqueous acid stripping mediums such as aqueous sulfuric acid (i.e. 25–100 g./l. H$_2$SO$_4$). The metal values are then desirably recovered from the aqueous stripping medium by electrolysis. The loaded organic can also preferably be stripped with fairly concentrated ammonia solutions. The loaded organic:aqueous stripping phase ratios can also vary widely. However, the over-all object of the process is to provide a metal containing stripping solution wherein the metal is present in higher concentrations than in the starting aqueous solution. Accordingly, the loaded organic aqueous stripping phase ratio will preferably be in the range of 1:1 to 10:1.

The following examples illustrate preferred embodiments of the extraction process of the present invention without being limiting.

EXAMPLE I

A series of extractions were carried out with the compounds of the present invention as well as with compounds outside of the scope of the invention. In these extractions, 0.1 M solutions of each $\beta$-diketone in Napoleum 470 (an aliphatic kerosene having a flashpoint — 175° F., boiling point —>400° F. — available from Kerr-McGee) are prepared. The solutions are each washed with 10% by weight sodium carbonate in water until no significant emulsification occurs (usually three or four washes were used). The organic layer was filtered and finally washed once with 10% sulfuric acid. The resulting solutions were then dried over anhydrous sodium sulfate.

Twenty milliliter portions of the organic solutions were then shaken for sixty minutes (at room temperature) in separatory funnels with 20 milliliter portions of an aqueous solution containing 0.2 M CuSO$_4$, 0.25 M NH$_3$, and 0.5 M (NH$_4$)$_2$CO$_3$. The resulting mixtures were then carefully watched during phase separation in order to observe any third phase formation. If, after standing at least 24 hours, any third phase formation occurred, the mixture was centrifuged and the supernatant organic was filtered and analyzed for copper by atomic absorption spectrophotometry. The resulting determination of copper concentration was then designated as [Cu]$_{max}$ for the particular $\beta$-diketone.

If no third phase was evidence, the copper loaded organic phase was shaken again for sixty minutes with a fresh 20 ml. portion of the ammoniacal aqueous copper solution. If no third phase was visible at this point, a 0.2 M solution of the $\beta$-diketone in Napoleum 470 was prepared and the entire procedure repeated. Such procedure was continued through 0.3 M, 0.4 M, and 0.5 M $\beta$-diketone solutions or until third phase formation was apparent. The concentration of soluble copper in the $\beta$-diketone solution which first forms a third phase is [Cu]$_{max}$. If there was no third phase in the 0.5 M $\beta$-diketone solution, [Cu]$_{max}$ was given as the soluble copper in the 0.5 M solution as a lower limit or minimum value (the values prefixed with the ">" symbol indicate that the [Cu]$_{max}$ is possibly greater than the value given in the table). Results are set forth in the following Table I:

Table 1

| Diketone of Example | Structure R | R' | [Cu] max (g./l. Cu++) |
|---|---|---|---|
| D | $C_{12}H_{25}-\phi-$ | $(CH_3)_3-C-\phi-$ | >18 |
| H | $C_{12}H_{25}-\phi-$ | $CH_3-\phi-$ | >13 |
| I | $C_9H_{19}-\phi-$ | $CH_3-\phi-$ | >11.6 |
| A | $C_{12}H_{25}-\phi-$ | $CH_3-$ | >12 |
| G | $C_9H_{19}-\phi-$ | $CH_3-$ | >11 |
| F | $\phi-$ | $C_7H_{15}-$ | >10 |
| E | $\phi-$ | $C_{17}H_{35}-$ | >12 |
| K | $C_{12}H_{25}-\phi-$ | (2-chlorophenyl) | >13.5 |
| J | $C_{12}H_{25}-\phi-$ | (2,6-dichlorophenyl) | >13.0 |
| M | $C_{12}H_{25}-\phi-$ | $C_7H_{15}-$ | >12.0 |
| B | $C_{12}H_{25}-\phi-$ | $C_8H_{17}-$ | >11.5 |
| C | $C_{12}H_{25}-\phi-$ | $C_7H_{15}-$ | >12.1 |
| Comparative | $t-C_4H_9-\phi-$ | $CH_3-\phi-$ | <1 |
| " | $C_{12}H_{25}-\phi-$ | $\phi-$ | ~2.7 |
| " | $\phi-$ | $\phi-$ | <1 |
| " | $t-C_4H_9-\phi-$ | $CH_3-$ | 0.1 |
| " | $\phi-$ | $CH_3-$ | <1 |
| " | $\phi-$ | $i-C_4H_9-$ | ~4.7 |
| " | $\phi-$ | $n-C_3H_7-$ | 0.5 |
| " | $\phi-$ | $i-C_3H_7-$ | 2.0 |
| " | $t-C_4H_9-$ | $t-C_4H_9-$ | ~2.4 |
| " | $t-C_4H_9-$ | $C_7H_{17}-$ | >6 |

EXAMPLE II

At least 100 ml. of 0.1 M Solutions in Napoleum 470 of the new β-diketones of the present invention as well as with compounds outside the scope of the invention were prepared as in Example I. Ten separate 10 ml. portions of each solution were then made up.

Another solution containing 8 M $NH_3$, 2 M $(NH_4)_2CO_3$ and 0.005 M $CuSO_4$ in water was prepared. This solution was diluted with increasing amounts of 0.005 M $CuSO_4$ in water to give ten solutions having a constant $Cu^{++}$ content but ranging from 1.2 M to 12 M in total ammonia. Total ammonia includes the ammonia present in solution as ammonium carbonate (the ratio of $NH_3/(NH_4)_2CO_3$ remained constant in all the solutions as 4/1).

The 10 ml. samples of the β-diketones were each shaken for 60 minutes with a 10 ml. sample of the varying ammoniacal copper solutions. After phase separation, the distribution of copper between the organic and aqueous phases was determined by atomic absorption spectrophotometry. A plot was then made for each extractant series of percent extraction vs. ammonia concentration. The $[NH_3]_{50}$ is set forth in the following Table II as read from the plots as the ammonia concentration at 50 percent copper extraction.

Table II

| Diketone of Example | Structure R | R' | $[NH_3]_{50}$ g./l. |
|---|---|---|---|
| B | $C_{12}H_{25}-\phi-$ | $C_8H_{17}-$ | 40 |
| D | $C_{12}H_{25}-\phi-$ | $(CH_3)_3-C-\phi-$ | 42 |
| C | $C_{12}H_{25}-\phi-$ | $C_7H_{15}-$ | 42 |
| F | $\phi-$ | $C_7H_{15}-$ | 47 |
| A | $C_{12}H_{25}-\phi-$ | $CH_3-$ | 50 |

Table II-continued

| Diketone of Example | Structure R | R' | $[NH_3]_{50}$ g./l. |
|---|---|---|---|
| K | $C_{12}H_{25}-\phi-$ | (2-chlorophenyl) | 63 |
| J | $C_{12}H_{25}-\phi-$ | (2,6-dichlorophenyl) | 76 |
| M | $C_{12}H_{25}-\phi-$ | $C_7H_{15}-$ | 84 |
| Comparative | $(CH_3)_3-C-$ | $(CH_3)_3-C-$ | 28 |
| " | $(CH_3)_3-C-$ | $C_7H_{15}-$ | 36 |
| " | $(CH_3)_2CH-$ | $(CH_3)_2CH-$ | 38 |
| " | $CH_3(CH_2)_3-$ | $CH_3(CH_2)_3-$ | 43 |
| " | $C_{12}H_{25}-\phi-$ | $\phi-$ | 46 |

EXAMPLE III

A number of extractions were carried out using the β-diketone of Example M. The organic and aqueous phases were shaken for 60 minutes at ambient temperatures and then analyzed for metal value content. The solvent for the β-diketone was Napoleum 470. The data is set forth in the following Table III:

Table III

| Aqueous Feed | | Conc. of Diketone (% by wt.) | O/A Phase Ratio | Org. Metal g./l. | Aq. Metal g./l. |
|---|---|---|---|---|---|
| Metal g./l. | $NH_3$ g./l. | | | | |
| $Cu^{++(1)}$ | | | | | |
| 10.6 | 25 | 20 | 1/2 | 10.85 | 10.6 |
| 3.1 | 5 | 4 | 1/5 | 1.70 | 2.88 |
| 3.1 | 5 | 4 | 1/2 | 1.77 | 2.36 |
| 3.1 | 5 | 4 | 1/1 | 1.75 | 1.59 |
| 3.1 | 5 | 4 | 2/1 | 1.53 | 0.18 |
| 3.1 | 5 | 4 | 5/1 | 0.67 | 0.00 |
| $Ni^{++(2)}$ | | | | | |
| 3.0 | 5 | 4 | 1/5 | 0.86 | 2.75 |
| 3.0 | 5 | 4 | 1/2 | 0.82 | 2.59 |
| 3.0 | 5 | 4 | 1/1 | 0.75 | 2.30 |
| 3.0 | 5 | 4 | 2/1 | 0.62 | 1.90 |
| 3.0 | 5 | 4 | 5/1 | 0.42 | 1.22 |

(1)$Cu^{++}$ derived from the addition of $CuSO_4$ to water
(2)$Ni^{++}$ derived from the addition of $NiSO_4$ to water Under essentially the same conditions $Zn^{++}$ (derived from $ZnSO_4$) was only extracted to the extent less than 5 ppm.

EXAMPLE IV

Copper was extracted with the β-diketone of Example D dissolved in Napoleum 470 (0.5 M or 22.4% by wt.). The extractions were conducted in essentially the same manner as those of Example III and the data is set forth in Table IV-a.

Table IV-a

| Aqueous Feed | | | O/A Phase Ratio | Org. $Cu^{++}$ g./l. | Aq. $Cu^{++}$ g./l. |
|---|---|---|---|---|---|
| $Cu^{++}$ (as $CuSO_4$) g./l. | $(NH_4)_2CO_3$ g./l. | $NH_3$ g./l. | | | |
| 13.1 | 50 | 25.0 | 1/1 | 11.9 | 1.14 |
| " | " | " | 2/1 | 6.44 | 0.03 |
| " | " | 27.0 | 1/1 | 10.5 | 2.00 |
| " | " | " | 2/1 | 6.35 | 0.17 |
| " | " | 37.9 | 1/1 | 9.1 | 3.35 |
| " | " | " | 2/1 | 6.05 | 0.82 |
| " | " | 60.0 | 1/1 | 6.96 | 5.60 |
| " | " | " | 2/1 | 5.07 | 2.92 |
| " | 100 | 30.9 | 1/1 | 11.3 | 1.62 |
| " | " | " | 2/1 | 6.40 | 0.01 |
| " | " | 40.0 | 1/1 | 10.1 | 2.49 |
| " | " | " | 2/1 | 6.57 | 0.43 |
| " | " | 60.2 | 1/1 | 7.34 | 5.33 |

Table IV-a-continued

| Aqueous Feed | | | | | |
|---|---|---|---|---|---|
| Cu++ (as CuSO$_4$) g./l. | (NH$_4$)$_2$CO$_3$ g./l. | NH$_3$ g./l. | O/A Phase Ratio | Org. Cu++ g./l. | Aq. Cu++ g./l. |
| " | " | " | 2/1 | 5.13 | 2.50 |
| " | " | 98.4 | 1/1 | 3.66 | 8.98 |
| " | " | " | 2/1 | 2.92 | 7.28 |

A loaded organic phase of the β-diketone as used in this Example (5.3 g./l. Cu++) was stripped by shaking for 60 minutes with various sulfuric acid containing stripping solutions. The data is set forth in Table IV-b.

Table IV-b

| Aqueous Strip Solution | | Stripped Organic Cu++ (g./l.) | |
|---|---|---|---|
| H$_2$SO$_4$ g./l. | Cu++ (as CuSO$_4$) g./l. | O/A of 1/1 | O/A of 1/2 |
| 24.5 | 40 | 1.53 | 0.0019 |
| 26.5 | 0 | 0.95 | 0.0006 |
| 48.8 | 40 | 0.77 | 0.0011 |
| 49.2 | 0 | 0.40 | 0.0001 |
| 73.5 | 40 | 0.56 | 0.0004 |
| 74.0 | 0 | 0.26 | 0.0005 |

EXAMPLE V

Extractions were carried out using the β-diketone of Example D (4.6% w/v in Napoleum 470) on ammoniacal aqueous feed solutions containing both Cu++ and Zn++ or Cu++ and Ni++ or Cu++ and cobalt. The organic and aqueous phases after separation (shaken for 60 minutes) were then analyzed and the data is set forth in the following Tables V-a, V-b and V-c.

Table V-a

| O/A Phase Ratio | Organic | | Aqueous | |
|---|---|---|---|---|
| | Cu++, g./l. | Zn++, g./l. | Cu++, g./l. | Zn++, g./l. |
| 1/2 | 2.08 | 0.0009 | 0.61 | 1.6* |
| 1/1 | 1.50 | 0.016 | 0.05 | 1.6* |
| 2/1 | 0.84 | 0.031 | 0.007 | 1.6* |

*By calculation

Table V-b

| O/A Phase Ratio | Organic | | Aqueous | |
|---|---|---|---|---|
| | Cu++, g./l. | Ni++, g./l. | Cu++, g./l. | Ni++, g./l. |
| 1/2 | 1.97 | 0.018 | 0.63 | 1.41 |
| 1/1 | 1.57 | 0.11 | 0.12 | 1.31 |
| 2/1 | 0.82 | 0.30 | 0.03 | 0.86 |

Table V-c

| O/A Phase Ratio | Organic | | Aqueous | |
|---|---|---|---|---|
| | Cu++, g./l. | Cobalt, g./l. | Cu++, g./l. | Cobalt, g./l. |
| 1/2 | 1.61 | 0.11 | 0.86 | 0.95 |
| 1/1 | 1.25 | 0.16 | 0.42 | 0.86 |
| 2/1 | 0.78 | 0.18 | 0.12 | 0.67 |

EXAMPLE VI

Extractions were carried out using the β-diketone of Example D (0.1 M in Napoleum 470) for various contact periods to determine the kinetics of the extraction. The aqueous feed contained 0.1 M CuSO$_4$ (5.21 g./l. Cu++), 0.4 M NH$_3$ and 0.07 M (NH$_4$)$_2$CO$_3$ (8 g./l. NH$_3$ total). The organic:aqueous phase ratio was 1:1. Results were as follows:

Table VI

| Time, sec. | Organic Cu++, g./l. | Aqueous Cu++, g./l. |
|---|---|---|
| 15 | 1.77 | 4.60 |
| 30 | 1.81 | 4.53 |
| 60 | 1.79 | 4.50 |
| 120 | 1.78 | 4.50 |
| 300 | 1.75 | 4.49 |
| 600 | 1.77 | 4.48 |

EXAMPLE VII

Stripping kinetics for a copper loaded organic (.1 M β-diketone of Example D in Napoleum 470--loaded with 1.47 g./l. Cu++) were determined by contacting portions of same at a 1:1 phase ratio for various time periods with an aqueous phase containing 75 g./l. sulfuric acid. Results are set forth in Table VII.

Table VII

| Time, sec. | Organic Cu++, g./l. | Aqueous Cu++, g./l. |
|---|---|---|
| 15 | 0.79 | 0.46 |
| 30 | 0.56 | 0.70 |
| 60 | 0.24 | 1.02 |
| 120 | 0.027 | 1.28 |
| 300 | 0 | 1.35 |

EXAMPLE VIII

Extractions were carried out for 60 minutes shaking using the β-diketone of Example K. The data is as follows:

Table VIII

| O/A Phase Ratio | Cu++ (g./l.) in Feed | | Cu++ (g./l.) in | |
|---|---|---|---|---|
| | Organic | Aqueous | Loaded Organic | Raffinate |
| 1/5 | 0(1) | 2.90(3) | 2.60 | 1.83 |
| 1/2 | 0 | 2.90 | 2.68 | 1.63 |
| 1/1 | 0 | 2.90 | 2.45 | 0.63 |
| 2/1 | 0 | 2.90 | 1.56 | 0.01 |
| 5/1 | 0 | 2.90 | 0.62 | 0.001 |
| 1/1 | 0(2) | 12.2(4) | 11.5 | 1.47 |
| 1/1 | 11.5 | 12.2 | 13.6 | 10.9 |
| 1/1 | 13.6 | 12.2 | 13.5 | 12.2 |

(1)4.3% wt./vol. of β-diketone in Napoleum 470
(2)21.5% wt./vol. of β-diketone in Napoleum 470
(3)Cu+$^{30}$ as CuSO$_4$, also contained 5 g./l. NH$_3$ and 7 g./l. (NH$_4$)$_2$CO$_3$
(4)Cu++ as CuSO$_4$, also contained 25 g./l. NH$_3$ and 50 g./l. (NH$_4$)$_2$CO$_3$

EXAMPLE IX

Extractions were carried out using the β-diketone of Example J (~0.1 M in Napoleum 470) and aqueous feed containing 3.1 g./l. Cu++ (as CuSO$_4$), 4.3 g./l. NH$_3$ and 6.7 g./l. (NH$_4$)$_2$CO$_3$. Contact time was 60 minutes. Table IX contains the results of these extractions.

Table IX

| O/A Phase Ratio | Organic Cu++, g./l. | Aqueous Cu++, g./l. |
|---|---|---|
| 1/5 | 2.54 | 2.61 |
| 1/2 | 2.41 | 1.92 |
| 1/1 | 2.40 | 0.67 |
| 2/1 | 1.54 | 0.007 |
| 5/1 | 0.60 | 0.0008 |

The β-diketone of Example J was also found to extract Cu++ selectively over Zn++ or Co+++ and Ni++ over Co+++.

EXAMPLE X

A copper loaded organic solution of the β-diketone of Example J (23% wt./vol. β-diketone in Napoleum 470, 14.3 g./l. Cu++ and 0.2 g./l. NH$_3$) was subjected to stripping at contact times of 60 min. with varying $H_2SO_4$ containing stripping solutions. Data is set forth in the following Table:

Table X

| Strip Solution | | Stripped Organic $Cu^{++}$, g./l. | |
|---|---|---|---|
| $H_2SO_4$, g./l. | $Cu^{++}$, g./l. | O/A Phase Ratio of 1/1 | O/A Phase Ratio of 1/2 |
| 24.5 | 40 | 2.92 | 0.35 |
| 26.5 | 0 | 2.33 | 0.06 |
| 48.8 | 40 | 0.73 | 0.04 |
| 49.2 | 0 | 0.46 | 0.08 |
| 73.5 | 40 | 0.14 | 0.11 |
| 74.0 | 0 | 0.08 | 0.09 |

EXAMPLE XI

Extractions and stripping operations were carried out with the β-diketone of Example M at contact times of 60 minutes. Table XI contains the data.

Table XI

| Extraction O/A Phase Ratio | Aqueous Feed $Cu^{++}$ g./l. | Organic Feed wt. % of β-diketone in Napoleum 470 | Loaded Organic $Cu^{++}$ g./l. | Aqueous Raffinate $Cu^{++}$ g./l. |
|---|---|---|---|---|
| 1/2 | 3.03[1] | 4 | 2.43 | 1.86 |
| 1/1 | 3.03 | 4 | 2.40 | 0.62 |
| 2/1 | 3.03 | 4 | 1.52 | 0.002 |
| 1/1 | 12.1[2] | 12 | 7.09 | 5.17 |
| 1/1 | 12.1 | 12[3] | 7.23 | 12.3 |

| Stripping O/A Phase Ratio | Aqueous Stripping Solution $H_2SO_4$, g./l. | Loaded[4] Organic wt. % β-diketone | Stripped Organic $Cu^{++}$, g./l. |
|---|---|---|---|
| 1/1 | 25 | 12 | 0.52 |
| 1/1 | 50 | 12 | 0.04 |
| 1/1 | 75 | 12 | 0.08 |

[1]$Cu^{++}$ as $CuSO_4$, also contained 7 g./l. $NH_3$
[2]$Cu^{++}$ as $CuSO_4$, also contained 25 g./l. $NH_3$
[3]also contained 7.09 g./l. $Cu^{++}$
[4]contained 7.23 g./l. $Cu^{++}$

EXAMPLE XII

A solution of 4.1% wt./vol. of the β-diketone of Example C in Napoleum 470 was loaded with $Ni^{++}$ (1.64 g./l.). It was then shaken for 60 min. with an equal volume of a solution prepared by dissolving 96 g. of ammonium carbonate per liter of concentrated aqueous ammonia. The stripped organic contained only 0.005 g./l. $Ni^{++}$. Distillation of the aqueous stripping medium would leave basic nickel carbonate as a residue.

In a similar manner a 21.4% wt./vol. solution of the β-diketone of Example C was loaded with 11.6 g./l. $Cu^{++}$ and then shaken for 60 minutes with the above ammonia stripping medium at an organic:aqueous phase ratio of 1:2. The stripped organic contained 0.25 g./l. $Cu^{++}$. The copper containing aqueous stripping medium could be distilled to leave CuO as a residue. The volatile $NH_3$, $CO_2$ and $H_2O$ could be condensed and recycled.

EXAMPLE XIII

An approximately 0.1 M solution of the β-diketone of Example A in Napoleum 470 was contacted for 60 minutes at varying phase ratios with an aqueous solution containing 2.85 g./l. $Cu^{++}$ (approximately 0.05 M $CuSO_4$, 0.2 M $NH_3$ and 0.07 M $(NH_4)_2CO_3$). The results are set forth in the following Table XII:

Table XII

| O/A Phase Ratio | Organic $Cu^{++}$, g./l. |
|---|---|
| 1/5 | 2.33 |
| 1/2 | 2.98 |
| 1/1 | 2.64 |
| 2/1 | 1.45 |
| 5/1 | 0.63 |

Similar extractions of a $Ni^{++}$ containing solution (3.09 g./l. $Ni^{++}$—0.5 M $NiSO_4$, 0.2 M $NH_3$ and 0.07 M $(NH_4)_2CO_3$) produced some emulsion problems. $Ni^{++}$ was extracted, however.

EXAMPLE XIV

Example XIII was essentially repeated except using the β-diketone of Example C. Results are set forth in the following Tables XIII and XIV.

Table XIII

| O/A Phase Ratio | Organic $Cu^{++}$, g./l. | Aqueous $Cu^{++}$, g./l. |
|---|---|---|
| 1/5 | 2.81 | 2.54 |
| 1/2 | 2.82 | 1.71 |
| 1/1 | 2.75 | 0.45 |
| 2/1 | 1.64 | 0.01 |
| 5/1 | 0.65 | 0.00 |

Table XIV

| O/A Phase Ratio | Organic $Ni^{++}$, g./l. | Aqueous $Ni^{++}$, g./l. |
|---|---|---|
| 1/5 | 2.29 | 2.36 |
| ½ | 2.16 | 1.76 |
| 1/1 | 1.93 | 1.00 |
| 2/1 | 1.29 | 0.40 |
| 5/1 | 0.57 | 0.15 |

The β-diketone of Example L at a 1/1 phase ratio gave similar results in the extraction of $Cu^{++}$ and $Ni^{++}$ (some emulsion problems were evident in respect of the aqueous $Ni^{++}$ phase.

EXAMPLE XV

A series of extractions (60 minute contact times — 1/1 phase ratios) were carried out using the β-diketone of Example A (3.3 wt./vol. % in Napoleum 470) wherein the pH was varied. Thus the aqueous solutions were made up of the hydrated metal salts and the solutions were diluted with either sulfuric acid or sodium hydroxide solutions of low concentration (less than 0.1 M). Results are set forth in Table XV.

Table XV

| $Cu^{++}$ Extraction | | |
|---|---|---|
| Raffinate pH | Organic $Cu^{++}$, g./l. | Aqueous $Cu^{++}$, g./l. |
| 2.7 | 0.06 | 2.63 |
| 2.9 | 0.15 | 2.54 |
| 3.3 | 0.45 | 2.24 |
| 3.8 | 1.31 | 1.38 |
| $Ni^{++}$ Extraction | | |
| Raffinate pH | Organic $Ni^{++}$, g./l. | Aqueous $Ni^{++}$, g./l. |
| 6.5 | 0.004 | 2.89 |
| 6.7 | 0.04 | 2.85 |
| 6.8 | 0.13 | 2.76 |
| 6.8 | 0.49 | 2.40 |

EXAMPLE XVI

Example XV was essentially repeated using the β-diketone of Example C (4.2% wt./vol. in Napoleum 470). Results were as follows:

Table XVI

Cu++ Extraction

| Raffinate pH | Organic Cu++, g./l. | Aqueous Cu++, g./l. |
| --- | --- | --- |
| 2.6 | 0.20 | 2.99 |
| 2.7 | 0.25 | 2.98 |
| 2.7 | 0.33 | 2.86 |
| 3.2 | 0.87 | 2.35 |
| 3.8 | 1.60 | 1.61 |
| 7.3 | 2.55 | 0.04 |

Ni++ Extraction

| Raffinate pH | Organic Ni++, g./l. | Aqueous Ni++, g./l. |
| --- | --- | --- |
| 6.5 | 0.004 | 2.91 |
| 6.8 | 0.06 | 2.82 |
| 6.8 | 0.17 | 2.79 |
| 6.7 | 0.76 | 2.19 |

EXAMPLE XVII

Extraction and stripping of Cu++ was carried out with the β-diketone of Example A (3.3% wt./vol. in Napoleum 470). Contact times equaled 60 minutes. Results were as follows:

Table XVII

| Cycle | Cu++ (g./l.) in Organic After Extraction[1] | Cu++ (g./l.) in Organic After Stripping[2] |
| --- | --- | --- |
| 1 | 2.50 | 0.0013 |
| 2 | 2.57 | 0.0006 |
| 3 | 2.62 | 0.0004 |
| 4 | 2.58 | 0.0008 |
| 5 | 2.49 | 0.0003 |
| 6 | 2.48 | 0.0002 |
| 7 | 2.18 | 0.0005 |
| 8 | 2.48 | — |
| 9 | 2.48 | 0.0003 |
| 10 | 2.50 | 0.0003 |

[1]The aqueous phase was 0.05 M $CuSO_4$, 0.2 M $NH_3$ and 0.07 M $(NH_4)_2CO_3$ in water and organic:aqueous phase ratio was ½.
[2]The strip solution was 100 g./l. sulfuric acid in water and the organic:aqueous stripping medium phase ratio was 10/1.

The embodiments of the invention in which an exclusive property or privilege is claimed are defined as follows:

1. A compound of the structure

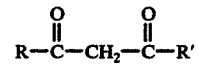

where R is phenyl and R' is a branched chain alkyl group of 7 to 20 carbon atoms.

2. The compound of claim 1 wherein R' is a branched chain heptyl group.

3. The compound of claim 1 wherein R' is a branched chain heptadecyl group.

* * * * *

UNITED STATES PATENT AND TRADEMARK OFFICE
CERTIFICATE OF CORRECTION

PATENT NO. : 4,065,502
DATED : Dec. 27, 1977
INVENTOR(S) : Kenneth D. MacKay and Edgar R. Rogier It is certified that error appears in the above-identified patent and that said Letters Patent are hereby corrected as shown below:

Columns 3 and 4, Table A, the heading - Mole Ratios - should be over columns 5, 6, and 7 of the table rather than over all Columns 3 and 4, Table A, column 3, line 3, of the table, "$(CH_3)_3O-\emptyset-$" should read - $(CH_3)_3C-\emptyset-$ -

Column 6, line 30, "62" should read - $\beta$ -

Column 10, line 43, "Cu+30" should read - $Cu^{++}$ -

Column 12, line 31, "½" should read - 1/2 -

Column 14, line 14, "½" should read - 1/2 -

Signed and Sealed this

Thirteenth Day of June 1978

[SEAL]

Attest:

RUTH C. MASON
Attesting Officer

DONALD W. BANNER
Commissioner of Patents and Trademarks